United States Patent
Cai et al.

(10) Patent No.: US 9,302,242 B2
(45) Date of Patent: Apr. 5, 2016

(54) PREPARATION OF NANOMETRIC ARRAYS OF BIOMOLECULES ON OLIGO- OR POLY(ETHYLENE GLYCOL) FILMS ON SILICON SURFACES

(75) Inventors: Chengzhi Cai, Houston, TX (US); Chi Ming Yam, Dallas, TX (US); Jianhua Gu, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 1819 days.

(21) Appl. No.: 11/587,232

(22) PCT Filed: Apr. 27, 2005

(86) PCT No.: PCT/US2005/014391
§ 371 (c)(1),
(2), (4) Date: Oct. 23, 2006

(87) PCT Pub. No.: WO2005/112565
PCT Pub. Date: Dec. 1, 2005

(65) Prior Publication Data
US 2007/0212555 A1    Sep. 13, 2007

Related U.S. Application Data

(60) Provisional application No. 60/566,120, filed on Apr. 28, 2004.

(51) Int. Cl.
*G01N 33/551* (2006.01)
*B01J 19/00* (2006.01)
(Continued)

(52) U.S. Cl.
CPC .......... *B01J 19/0046* (2013.01); *G01N 33/552* (2013.01); *B01J 2219/00317* (2013.01); *B01J 2219/00351* (2013.01); *B01J 2219/00436* (2013.01); *B01J 2219/00527* (2013.01); *B01J 2219/00605* (2013.01); *B01J 2219/00612* (2013.01); *B01J 2219/00617* (2013.01); *B01J 2219/00621* (2013.01); *B01J 2219/00626* (2013.01); *B01J 2219/00637* (2013.01); *B01J 2219/00659* (2013.01);
(Continued)

(58) Field of Classification Search
CPC ................ G01N 33/552; B01J 19/0046; B01J 2219/00605; B01J 2219/00529; B01J 2219/0061; B01J 2219/00612; B01J 2219/00617; B01J 2219/00621; B01J 2219/00626; B01J 2219/00637; B01J 2219/00659; B01J 2219/00
See application file for complete search history.

(56) References Cited

U.S. PATENT DOCUMENTS

| 5,973,124 | A | 10/1999 | Bayer et al. |
| 6,183,990 | B1 * | 2/2001 | Duecker et al. ............. 435/69.1 |
| 6,677,163 | B1 * | 1/2004 | Boukherroub et al. ......... 506/17 |

OTHER PUBLICATIONS

Yang et al. Protein intecracitons with poly(ethylene glycol) self-assembled monolayers on glass substrates: diffusion and adsorption. Langmuir 1999, vol. 15, pp. 8405-8411.*

(Continued)

*Primary Examiner* — Shafiqul Haq
(74) *Attorney, Agent, or Firm* — Winstead PC (57) ABSTRACT

The present invention is generally directed to nanometric biomolecular arrays and to a novel approaches for the preparation of such nanoarrays, based on binding of biomolecules, such as avidin, to templates generated by lithographically-anodizing biocompatible ultrathin films on silicon substrates using AFM anodization lithography. The present invention is also directed to methods of using such arrays.

12 Claims, 5 Drawing Sheets

(51) Int. Cl.
*G01N 33/552* (2006.01)
*B82Y 30/00* (2011.01)
*B82Y 40/00* (2011.01)
*G01Q 80/00* (2010.01)

(52) U.S. Cl.
CPC .......... *B01J 2219/00722* (2013.01); *B01J 2219/00725* (2013.01); *B82Y 30/00* (2013.01); *B82Y 40/00* (2013.01); *G01Q 80/00* (2013.01)

(56) References Cited

OTHER PUBLICATIONS

Gu et al. Nanometric protein arrays on protein-resistant monolayers on silicon surfaces. J. Am. Chem. Soc. 2004, vol. 126, pp. 8098-9099.*

Gu, Jianhua, et al., "Nanometric protein arrays on protein-resistant monolayers on silicon surfaces," Journal of the American Chemical Society, Jul. 7, 2004, vol. 126, No. 26, pp. 8098-8099.

Ciampi, Simone, et al., "Functionalization of acetylene-terminated monolayers on Si(100) surfaces: a click chemistry approach," Langmuir: The ACS Journal of Surfaces and Colloids, Aug. 28, 2007, vol. 23, No. 18, pp. 9320-9329.

Rohde, et al., "Non-Oxidative Approach toward Chemically and Electrochemically Functionalizing Si(111)," J. Am. Chem. Soc., vol. 128, Jan. 1, 2006, pp. 9518-9525.

Meldal, Morten, et al., "Cu-catalyzed azide-alkyne cycloaddition," Chemical Reviews, Aug. 2008, vol. 108, No. 8, pp. 2952-3015.

Svedhem et al., "Synthesis of a Series of Oligo(ethylene glycol)-terminated Alkanethiol Amides Designed to Address Structure and Stability . . . ", 66 J. Org. Chem. (2001), pp. 4494-4503.

Yam et al., "Modification of Silicon AFM Cantilever Tips with an Oligo(ethylene glycol) Derivative for resisting Proteins . . . ", 125 J. Am.Chem. Soc. (2003), pp. 7498-7499.

Stewart et al., "Photopatterned Hydrosilylation on Porpous Silicon", 37(23) Angew. Chem. Int. Ed. (1998), pp. 3257-3260.

Maoz et al., "Constructive Nanolithography: Inert Monolayers as Patternable Templates . . . ", 12(10) Adv. Mater. (2000), pp. 725-731.

Seidel et al., "Miniaturization and parallelization of fluorescence immunoassyas in nanotiter plates", 22(6) Trends in Analytical Chemistry (2003), pp. 385-394.

International Preliminary Report on Patentability, PCT/US2005/014391, dated Nov. 9, 2006.

Linford, et al., "Alkyl Monolayers on Silicon Prepared from 1-Alkenes and Hydrogen-Terminated Silicon," 117 Am. Chem. Soc. 3145 (1995).

Cicero, et al., "Photoreactivity of Unsaturated Compounds with Hydrogen-Terminated Silicon (111)," 16 Langmuir 5688 (2000).

* cited by examiner

PREPARATION OF NANOMETRIC ARRAYS OF BIOMOLECULES ON OLIGO- OR POLY(ETHYLENE GLYCOL) FILMS ON SILICON SURFACES

CROSS-REFERENCE TO RELATED APPLICATIONS

This Application claims priority to U.S. Provisional Application Ser. No. 60/566,120, filed Apr. 28, 2004.

This invention was made, in part, with support from the National Science Foundation, Grant Number CTS-0210840; and the Robert A. Welch Foundation, Grant Number 1-5-57897.

FIELD OF THE INVENTION

This invention relates generally to microarrays, and specifically to nanometric biomolecular arrays and their fabrication.

BACKGROUND OF THE INVENTION

Microarray technology has been widely used for genomics and proteomics research as well as for drug screening. Currently, the spot size in most microarrays is larger than one micron. The use of nanometric biomolecular arrays, with smaller spot sizes, will enable high-throughput screening of biomolecules—eventually at the single molecule level. Also, nanometric arrays permitting precise control over the position and orientation of individual molecules will become a powerful tool for studying multi-valent and/or multi-component molecular interactions in biological systems. Toward these ends, protein arrays with feature sizes smaller than 100 nm have been fabricated, mostly using dip-pen nanolithography and nanografting. See Lee et al., Science 2002, vol. 295, p. 1702; Wilson et al., Proc. Natl. Acadi Sci. USA 2001, vol. 98, p. 13660; Liu et al., Proc. Natl. Acad. Sci. USA 2002, vol. 99, p. 5165; Pavlovic et al., Nano Lett. 2003, vol. 3, p. 779; and Krämer et al., Chem. Rev. 2003, vol. 103, p. 4367.

Biological microelectromechanical systems (bioMEMS) are of tremendous interest for their potential applications in microscale, high throughput biosensing and medical devices (Shawgo et al., J. Curr. Opin. Solid State Mater. Sci. 2002, v. 6, p. 329). Using silicon as a substrate for the preparation of such devices is particularly attractive, since the extensive micro-fabrication techniques developed by the microelectronic industries can be used to fabricate and integrate various micro-components into the devices. For reducing biofouling, considerable research has been directed to the modification of substrate surfaces with stable and ultrathin films of poly(ethylene glycol) (PEG) or oligo(ethylene glycol) (OEG) (Prime et al., Science 1991, vol. 252, p. 1164). Since many of the ultimate applications for bio-devices require moderate-term (e.g., a few hours to several days) exposure to biological media (e.g., buffer of pH 7.4 at 37° C.), stability of the bio-compatible coatings on the devices under these conditions is highly desirable. All of the OEG/PEG-terminated films on silicon substrates reported by others are bound onto the silicon surfaces via Si—O bonds that are prone to hydrolysis (Calistri-Yeh et al., Langmuir 1996, v. 12, p. 2747), thereby limiting their stability under physiological conditions (Sharma et al., Langmuir 2004, v. 20, p. 348).

As described in commonly assigned, co-pending U.S. patent application Ser. No. 10/742,047, olig(ethylene glycol) (OEG) terminated alkenes were grafted onto hydrogen-terminated silicon surfaces through hydrosilylation (as developed by Linford and Chidsey, see Linford et al., J. Am. Chem. Soc. 1993, v. 115, p. 12631; Buriak, Chem. Rev. 2002, v. 102, p. 1271) forming robust Si—C bonds with the silicon surfaces. It was shown that the alkyl monolayers grown by this method were stable in boiling organic solvents, water, and acids, as well as slightly basic solutions (Linford et al., J. Am. Chem. Soc. 1995, v. 117, p. 3145). A method describing the modification of hydrogen-terminated silicon surfaces, including a silicon atomic force microscopy (AFM) cantilever tip, with OEG-terminated alkenes via either thermally- or photo-induced hydrosilylation is also found in commonly assigned, co-pending U.S. patent application Ser. No. 10/742,047. See also Yam et al., J. Am. Chem. Soc. 2003, v. 125, p. 7498; Yam et al., Chem. Commun., 2004, p. 2510). The efficiency with which such OEG-terminated films resist protein adsorption depends on many factors including the number of ethylene glycol (EG) units and the packing density of the films that is determined by the underlying substrate surface and the deposition methods. For example, OEG-terminated thiolate self-assembled monolayers (SAMs) on gold (111) surfaces are protein resistant, but those on silver (111) surfaces are not (Herrwerth et al., J. Am. Chem. Soc. 2003, vol. 125, p. 9359). The latter was attributed to the high packing density and structural ordering of the SAMs. Research has demonstrated that films grown on Si (111) surfaces had a density similar to that of the corresponding thiolate SAMs on gold (111) surfaces, and similarly reduced the adsorption of fibrinogen to 1% monolayer or less (Cai et al., to be submitted).

As a result of the foregoing, a nanometric biomolecular array comprising a stable, patternable monolayer surface, and an efficient method of making such an array, would be very beneficial.

BRIEF DESCRIPTION OF THE INVENTION

The present invention is generally directed to a nanometric biomolecular array, and to methods of making such arrays, wherein such methods typically involve AFM anodization lithography. The present invention is also directed to methods of using such arrays.

In some embodiments, such above-mentioned methods generally comprise the steps of: (a) contacting OEG-terminated alkenes with a hydrogen-terminated Si surface to form a contacted surface; (b) photolyzing the contacted surface to effect Si—C bonding between the OEG-terminated alkenes and the Si surface and form an OEG-coated Si surface comprising a monolayer of OEG bound to the Si surface through Si—C bonds; (c) anodizing regions on the top of the OEG monolayer of the OEG-coated Si surface via AFM anodization lithography to yield a nanolithographically-patterned OEG-coated Si surface comprising regions with enhanced associability toward biomolecules; and (d) depositing at least one type of biomolecule in the regions of enhanced associability to form a nanometric biomolecular array.

Generally, the nanometric biomolecular arrays made by the above-described methods comprise: (a) a Si substrate; (b) a monolayer of OEG bonded to the Si substrate via Si—C bonds, wherein regions at the top of the monolayer have been lithographically-patterned; and (c) biomolecules associated with the lithographically-patterned regions of the OEG monolayer.

In some embodiments, the present invention provides a novel approach for preparation of uanometric protein arrays, based on binding of biomolecules to nano-templates generated by AFM anodization lithography on robust, ultrathin monolayers terminated with oligo(ethylene glycol) (OEG)

derivatives with the general formula of —(CH$_2$CH$_2$O)$_n$—R (n>1, R=CH$_3$, H, etc.) on conducting silicon surfaces. A specific example is the preparation of nanometric avidin arrays. Applicants have shown that biotinated-BSA, but not the native BSA, binds to the avidin arrays, and the resulting arrays of biotinated-BSA can bind avidin to form protein dots with a feature sizes of ~30 nm, scalable down to the size of a single protein molecule.

Such nanometric arrays have at least the following unique advantages: (a) they will vastly improve the detection sensitivity (down to a single molecule), allowing for detection of biomolecular variations correlated with diseases, which are typically expressed at very low level; (b) they will tremendously increase the probe density on a chip (e.g., incorporating the whole human genome in the same chip); (c) they permit a label-free detection of the binding of target molecules on the nanoarrays; (d) they greatly shorten the time for binding of target molecules to the nanoarrays and improve the efficiency of the binding; (e) they may substantially improve the specificity of the detection; (f) the single molecule arrays will greatly facilitate single molecule sequencing of DNA using polymerase and nucleotides that are fluorescently labeled, and single molecule arrays of the template and the polymerase will reduce the background fluorescence and greatly improve the quality of the data; and such (g) nanometric arrays will become a powerful research tool for studying the cooperative interaction among multiple biomolecules. It should be noted that advantages (a)-(e) can be gained only for nanoarrays where the spot size is less than about 25 nm and comprising only one or a handful of probe molecules.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The present invention is generally directed to nanometric biomolecular arrays and to a novel approaches for preparation of such nanoarrays, based on binding of biomolecules, such as avidin, to templates generated by AFM anodization lithography (conductive AFM) on biocompatible ultrathin films on silicon substrates. In some embodiments, such films are generally robust, ultrathin monolayers terminated with oligo(ethylene glycol) (OEG) with the general formula of —(CH$_2$CH$_2$O)$_n$—R (n>1, R=CH$_3$, H, etc.) on conducting silicon surfaces, wherein such films have been nanolithographically-patterned using conductive AFM lithography (Maoz et al., *Adv. Mater.* 2000, vol. 12, p. 725). The lithography process is followed by chemical and biochemical derivatization of the resulting nanopatterns. The unique features of this approach include: (a) the OEG-monolayers resist non-specific adsorption and denaturing of proteins on the templates; (b) conductive AFM can be used to selectively oxidize the top portion of the OEG-monolayer to generate carboxylic acids, aldehydes, alcohols and other functional groups that can be used to attach biomolecules; (c) the monolayers are attached to silicon substrates via Si—C bonds with a high density, rendering the system highly robust; and (d) the lithography process is very rapid. In a specific example, the resulting avidin arrays have a feature size of ~26 nm, and they can serve as templates for the preparation of nanoarrays of a wide variety of proteins that are site-specifically labeled with biotin (Lue et al., *J. Am. Chem. Soc.* 2004, v. 126, p. 1055).

Figure 1:
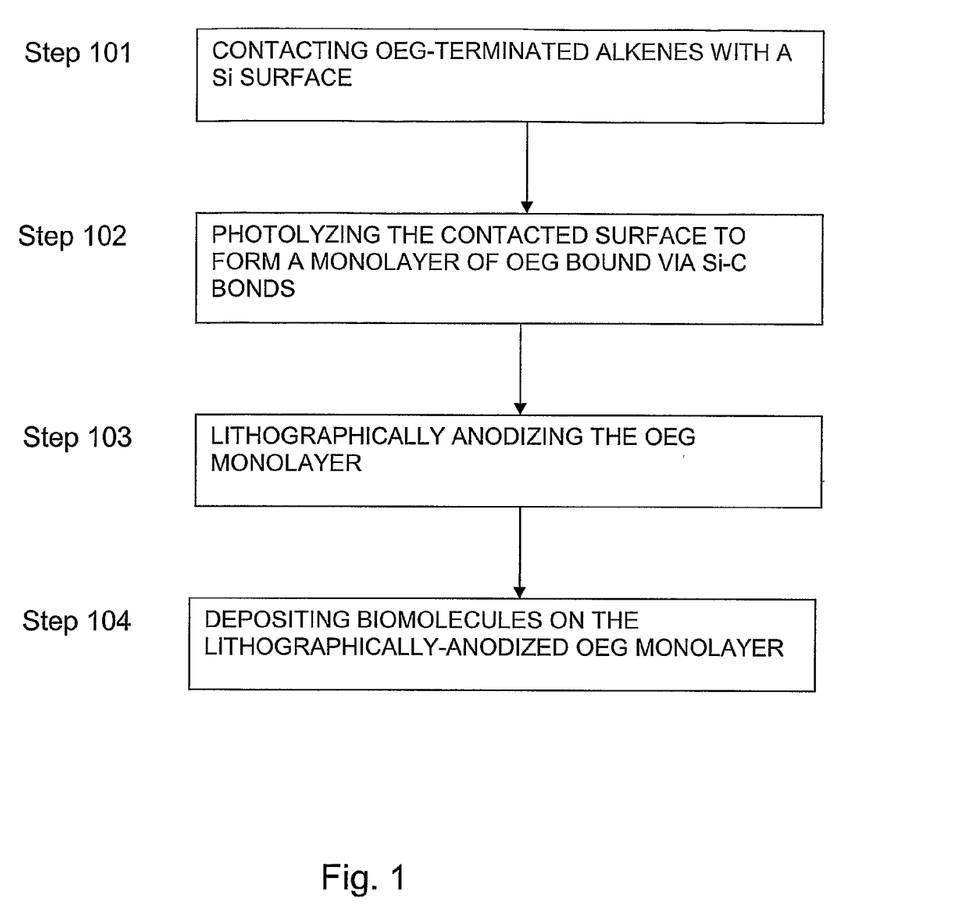
FIG. 1 depicts, schematically, a method of making nanometric biomolecular arrays, in accordance with embodiments of the present invention.

Referring to FIG. 1, in some embodiments, such above-mentioned methods generally comprise the steps of (Step 101) contacting OEG-terminated alkenes with a hydrogen-terminated Si surface to form a contacted surface; (Step 102) photolyzing the contacted surface to effect Si—C bonding between the OEG-terminated alkenes and the Si surface and form a OEG-coated Si surface comprising a monolayer of OEG bound to the Si surface through Si—C bonds; (Step 103) lithographically anodizing regions on the top of the OEG monolayer of the OEG-coated Si surface via AFM anodization lithography to yield a nanolithographically-patterned OEG-coated Si surface comprising regions with enhanced associability toward biomolecules; and (Step 104) depositing at least one type of biomolecule in the regions of enhanced associability to form a nanometric biomolecular array.

In some embodiments, the OEG-terminated alkenes comprise EG sequences selected from the group consisting of EG$_1$-EG$_{20}$, and combinations thereof, wherein "n" in EG$_n$ describes the number of —(CH$_2$CH$_2$O)— repeat units. In some or other embodiments, the OEG-terminated alkenes comprise PEG-terminated alkenes, wherein PEG-terminated alkenes comprise EG$_n$ sequences of n>20.

Typically, the Si surface is atomically flat. In some embodiments the Si surface is selected from the group consisting of (100), (111), and combinations thereof. In some embodiments, upon coating the Si surface with an OEG monolayer, the OEG-coated Si surface is washed, and optionally dried, prior to lithographically anodizing regions on top of it.

In some embodiments, the nanolithographically-patterned (anodized) regions of the OEG-coated Si surface comprise nanowells (i.e., "spots"). In some embodiments, the nanolithographically-patterned regions of the OEG-coated Si surface comprise carboxylic acid, aldehyde, alcohol, and/or other moieties, wherein these moieties provide, at least in part, the enhanced associability toward biomolecules.

In some embodiments, the at least one type of biomolecule is selected from the group consisting of proteins, oligonucleotides, and combinations thereof. Avidin is an exemplary such biomolecule. In some embodiments, at least some of the at least one type of biomolecule binds with the regions of enhanced associability via amide bonds.

Generally, the nanometric biomolecular arrays made by the above-described methods comprise: (a) a Si substrate; (b) a monolayer of OEG bonded to the Si substrate via Si—C bonds, wherein regions at the top of the monolayer have been lithographically-patterned; and (c) biomolecules associated with the lithographically-patterned regions of the OEG monolayer.

Typically, the above-mentioned Si surface is atomically flat. In some embodiments, the Si surface is selected from the group consisting of (100), (111), and combinations thereof. In some embodiments, the OEG bound to the Si surface comprises EG sequences selected from the group consisting of $EG_1$-$EG_{20}$, and combinations thereof. As mentioned above, such OEG is bound to the surface through Si—C bonds.

In some embodiments, the biomolecules (as part of the array) are selected from the group consisting of proteins, oligonucleotides, and combinations thereof. Avidin is an exemplary such molecule. Typically, the biomolecules are associated by a bonding means selected from the group consisting of covalent bonding, ionic bonding, electrostatic forces, and combinations thereof. In some particular embodiments, the biomolecules are associated with the lithographically-patterned regions of the OEG monolayer via amide bonds.

In some embodiments, the nanometric biomolecular array is operable for binding biomolecular analyte, i.e., it can be used to assay biomolecular analyte, wherein biomolecular analyte can comprise one or more of a variety of different biomolecules. In such embodiments, biomolecular analyte is deposited on the array, and the array is analyzed to determine the regions in which the biomolecular analyte exhibits a binding affinity. In some such embodiments, the biomolecules and biomolecular analyte are removed by treatment with proteinase K, wherein the proteinase K serves to catalyze hydrolytic fragmentation of proteins bound to the patterned OEG monolayer surface to regenerate the pattern. Biomolecular analyte suitable for such analysis (including sequencing) include, but are not limited to, oligonucleotides, proteins, and combinations thereof. In some or other embodiments, such an array is useful for screening drug candidates.

Figure 2:
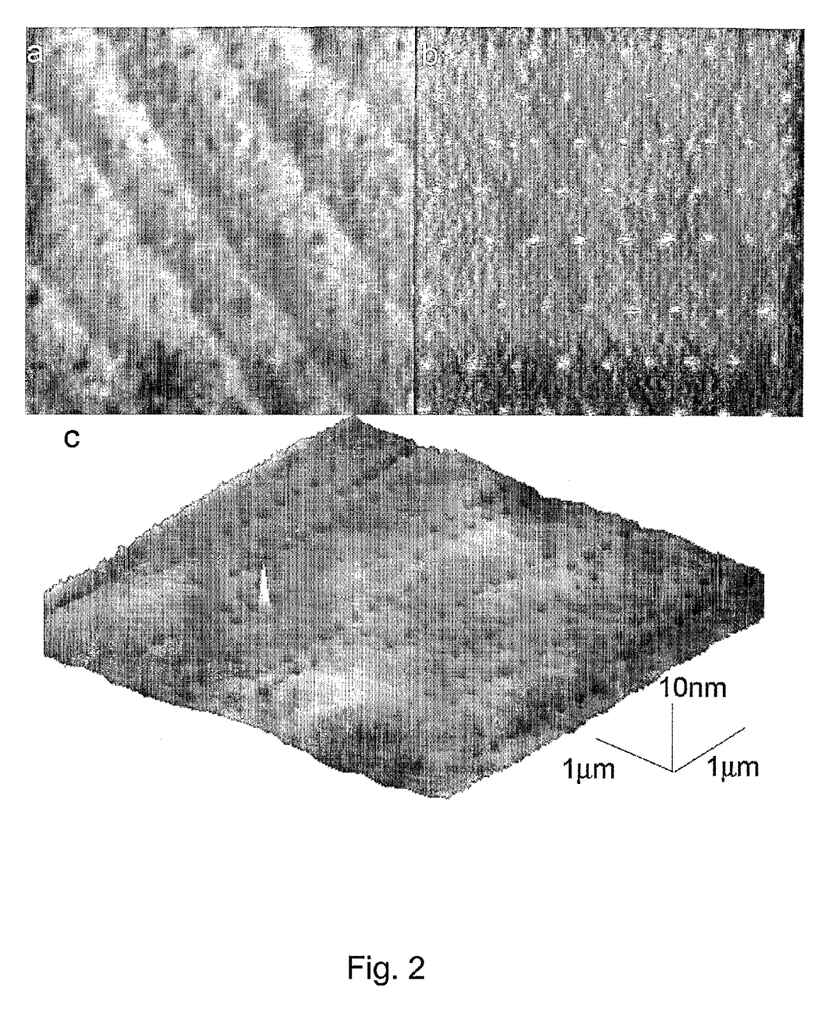
FIG. 2 depicts height (2$a$, 0.5×0.5 µm$^2$, 10 nm contrast) and friction (2$b$, 0.1 V contrast) AFM images of an EG$_7$ film on Si (111) after AFM anonization lithography, and a 3-dimensional image (2$c$, 5×5 µm$^2$) of a patterned area upon treatment with succinic anhydride, DMAP and pyridine.

The monolayers described herein can be readily prepared from α-hepta-(ethylene glycol) methyl ω-undecenyl ether, comprising seven EG ($EG_7$) repeat units (the term "$EG_7$" being used herein to describe both the repeat units and the alkene precursor comprising the seven EG repeat units), and conductive silicon (111) substrates with an atomically-flat, H-terminated surface (Yam et al., Chem. Commun., 2004, p. 2510). In accordance with some embodiments, AFM anodization lithography on these monolayers was performed under ambient conditions with a relative humidity of ~20-80%, using a Nanoscope IIIa AFM (Digital Instrument) equipped with a pulse generator. During AFM anodization on each location, a short pulse of +(4 to 17) V, with a duration typically in the range of about 10 nanoseconds (ns) to about 10 microseconds, was applied to the sample while the tip was grounded During AFM anodization, the AFM scanner can rapidly position the AFM tip on the sample with nanometer precision. This process for generating a high-density nanoarray proved to be much faster than dip-pen or nanografting lithography techniques that normally take seconds to generate each nanospot. The pulse generator was then disconnected, and height and friction AFM images were simultaneously acquired in contact mode at a 90° scan angle with the same tip. In one specific example, in which the nanolithography was performed with 100 ns pulses of +10 V, it was found that holes with an apparent depth of 0.4 nm (corresponding to the length of one ethylene glycol unit) were generated, as revealed by the height images of the patterned areas, e.g., FIG. 2a However, the corresponding friction image (FIG. 2b) shows the presence of spots of ~10 nm in diameter where the friction is higher than the surroundings, indicating the presence of polar head groups on the spots. Referring to FIG. 2, the spacing between the spots was ~50 nm, as controlled by the scanner.

While not intending to be bound by theory, it has been suggested that AFM anodization of alkyl siloxane monolayers on silicon under certain conditions could oxidize the head groups of the monolayers into carboxylic (COOH) groups (Maoz et al., J. Adv. Mater. 2000, v. 12, p. 725). However, a recent study of a similar system using secondary ion mass spectroscopy showed no signs of COOH groups on the oxidized surfaces (Pignataro et al., Mater. Sci. Eng. C. 2003, v. 23, p. 7).

Figure 3:
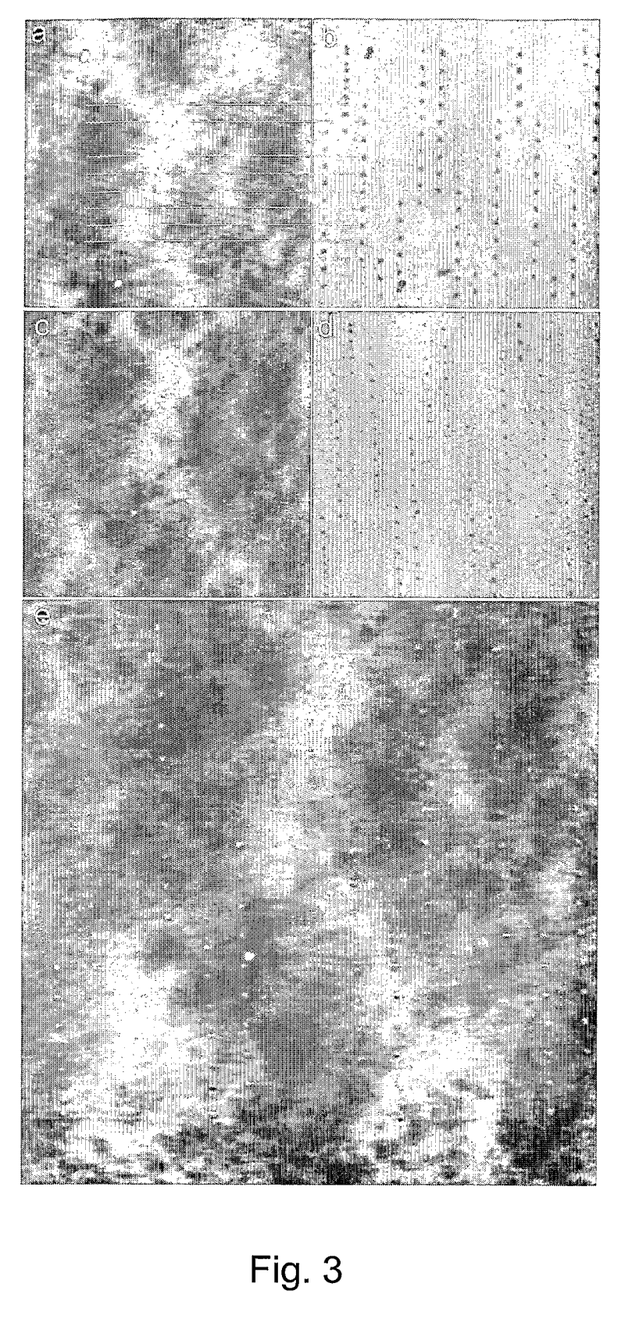
FIG. 3 depicts AFM height (3$a$, 3$c$, and 3$e$) and friction (3$b$ and 3$d$, corresponding to 3$a$ and 3$c$) images (4×4 µm$^2$) of an area similar to that shown in FIG. 2$c$ upon sequential treatment with EDAC/avidin (3$a$-$b$), biotinated-BSA (3$c$-$d$), and avidin (3$e$), wherein the lines in 3$a$-$b$ are used as guides.

It should be noted that the monolayers in the above-described study had alkyl head groups, while the monolayers of the present invention comprise an OEG head group. The AFM anodization of the OEG-coated surfaces could be substantially different from the above-described alkyl surfaces. Preliminary studies by Applicants indicate that, upon AFM anodization of OEG-coated surfaces, a variety of species including carboxylic acids, aldehydes, and alcohols, are generated on the film surface. Additionally, in some embodiments, treatment of an AFM-anodized monolayer with avidin is done in the presence of 1-ethyl-3-(3-dimethylaminopropyl)-carbodiimide (EDAC, which serves to mediate the formation of amide bonds between the surface COOH groups and the protein molecules). Corresponding AFM images obtained during the first few scans showed that the protein molecules predominately adsorbed on the patterned spots. The protein molecules were readily removed by the scanning tip afterwards indicating that the protein molecules were not covalently bound to the surface. Again, while not intending to be bound by theory, it was concluded that rather than COOH groups, the surfaces of the oxidized spots mainly comprised hydroxyl groups that could be chemically converted into COOH groups, e.g., by treatment with succinic anhydride, dimethyl-aminopyridine (DMAP) and pyridine. Patterned spots were "etched" upon this treatment forming nanoholes as shown by the three-dimensional AFM height image (FIG. 2c). As measured by the line profile of about 100 patterned spots in FIG. 2c, the diameter of the holes was 91±6 nm, and the depth was 1.31±0.12 nm, about one third of the thickness of the film. Using the method described herein, COOH groups were generated in the nanoholes, which may be used to attach proteins. Upon incubation of the samples with EDAC followed by avidin in PBS solution, the nanoholes were nearly filled (FIG. 3a) and barely recognized even by comparison with the corresponding friction image (FIG. 3b). The depth of the holes decreased to 0.43±0.06 nm, while the width of the holes remained nearly the same (87±9 nm).

The sample was then treated with BSA in PBS buffer. The depth of the holes remained the same, indicating that BSA did not bind to the molecules in the holes. To verify that the molecules in the holes were indeed avidin, the sample was treated with a solution of biotinated-BSA in PBS buffer. AFM height and friction images (FIG. 3c and 3d) reveal that the patterned spots protrude slightly from the film surface. The height and half-height width of the spots were 0.14±0.14 nm and 24±3.5 nm, respectively. The fact that the molecules in the holes bound biotinated-BSA but not native BSA is a strong indication that these molecules were avidin.

Figure 4:
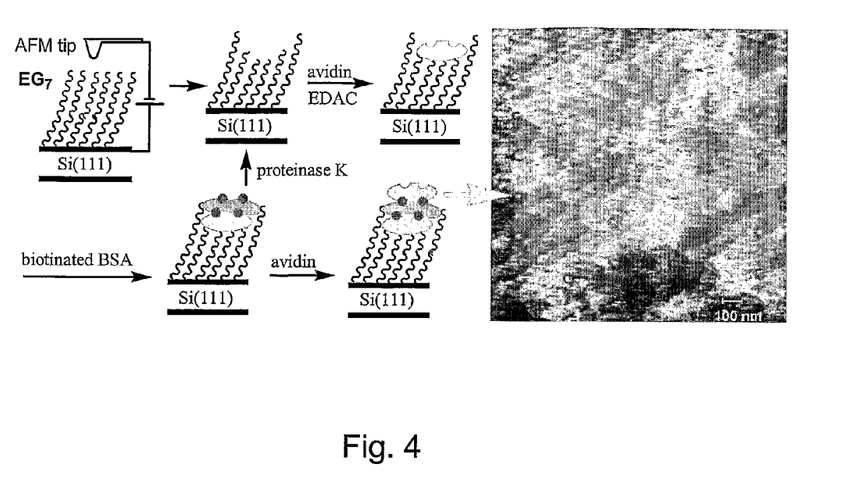
FIG. 4 demonstrates, schematically, a nanofabrication process, in accordance with embodiments of the present invention.

The patterned biotinated-BSA, with an average of nine biotin groups on each BSA molecule, should have free biotin groups available for binding additional avidin onto the pattern. Indeed, upon incubation of the sample in a solution of avidin in PBS, nano-dots arrays were formed, as shown by the AFM height image (FIG. 3e). The heights of the dots were 1.27±0.37 nm and the half-height widths of the dots were 26±3.4 nm. While the top avidin molecules could be removed by repeated scanning, the protein molecules in the holes were strongly bound, and could not be removed by the scanning tip, neither by immersion in PBS for 6 hours nor in detergent (SDS) solutions for 14 hours. AFM images of the protein arrays remained nearly the same after four weeks under ambient conditions. Upon treatment with Proteinase K (to catalyze the hydrolytic fragmentation of the proteins), nanoholes very similar to those in FIG. 2c were regenerated. The nanofabrication process, in accordance with some embodiments of the present invention, is demonstrated in FIG. 4.

Nanometric biomolecular array fabrication, as described herein and in accordance with embodiments of the present invention, will vastly improve the detection sensitivity (down to a single molecule), greatly facilitate single molecule sequencing of DNA, and serve as a powerful research tool for studying the cooperative interaction among multiple biomolecules.

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

This example serves to illustrate materials used in the fabrication of nanometric protein arrays, on protein-resistant monolayers on silicon surfaces, in accordance with embodiments of the present invention.

Pyridine, succinic anhydride, 4-dimethylaminopyridine (DMAP), 1-ethyl-3-(3-dimethylaminopropyl)-carbodiimide (EDAC), avidin, bovine serum albumin (BSA), biotinamidocaproyl labeled BSA (biotin-BSA), proteinase K, and phosphate buffered saline (PBS buffer, 0.01 M phosphate, 0.14 M NaCl, pH 7.4) were purchased and were used without purification.

EXAMPLE 2

This example serves to illustrate the synthesis of hepta (ethylene glycol) methyl ω-undecenyl ether (comprising $EG_7$), as used in some embodiments of the present invention.

Monomethyl hepta(ethylene glycol) (1.637 g, 4.81 mmol) was slowly added to NaH (0.81 g, 33.75 mmol) in dry THF (8 ml) while stirring under $N_2$. To this mixture was added $Bu_4NI$ (0.81 g, 0.48 mmol) and 11-bromo-1-undecene (4.2 ml, 16.78 mmol), and the mixture was refluxed for 20 hours under $N_2$. Iodomethane (3.42 g, 24.1 mmol) was added, and the mixture was refluxed for 1 hour. The reaction mixture was then refluxed with methanol for another hour. After cooling to room temperature, the mixture was concentrated under reduced pressure. Dichloromethane was added, and the mixture was subsequently poured into water. The organic layer was separated, and the aqueous layer was extracted twice with dichloromethane. The combined organic layers were washed twice with water, dried with magnesium sulfate, filtered and concentrated under reduced pressure. The crude product was purified by flash chromatography (ethyl acetate/hexane/methanol 50:48:2) to afford $EG_7$ (1.8 g, 76%). $^1$H NMR ($CDCl_3$): δ=5.80-5.82 (m, 1H); 4.90-5.01 (m, 2H); 3.52-3.65 (m, 26H); 3.41-3.46 (t, 2H); 3.37 (s, 3H); 2.02-2.04 (q, 2H); 1.54-1.57 (m, 4H); 1.30-1.36 (m, 12H). $^{13}$C NMR ($CDCl_3$): δ=139.35, 114.22, 72.06, 71.67, 70.70, 70.65, 70.18, 59.17, 33.93, 29.76, 29.67, 29.60, 29.55, 29.25, 29.05, 26.21. ESI-MS: 516.5 (100%, M+1+$Na^+$).

EXAMPLE 3

This example serves to illustrate photo-induced surface hydrosilylation, in accordance with embodiments of the present invention.

H-terminated silicon (100 or 111) surfaces were prepared using procedures similar to those described by Hines and Chidsey (Krämer et al., Chem. Rev. 2003, vol. 103, p. 4367). Briefly, single-sided polished silicon (100) or silicon (111) wafers with a resistivity less than 5 ohm·cm were cut into pieces of ca. 1×1 $cm^2$, cleaned with $NH_4OH/H_2O_2/H_2O$ (v/v 1:1:4) at 80° C. for 20 minutes, thoroughly washed with Millipore-purified water, etched in 10% buffer-HF for 10 minutes and then in 40% $NH_4F$ for 10 minutes under $N_2$ purge, and dried with a flow of nitrogen. The setup and procedures for photo-induced surface hydrosilylation of H-terminated silicon substrate surfaces with alkenes were described in detail elsewhere (Yam et al., Chem. Commun., 2004, p. 2510). Briefly, a freshly prepared H—Si (100) or H—Si (111) substrate was placed inside a freshly cleaned and dried quartz cell, and tilted with the polished surface facing a droplet (~1 mg) of the alkene ($EG_7$) that was placed on a surface in the cell. After the cell was degassed at ~0.1 mTorr for 10 minutes, the wafer was allowed to fall down onto the droplet, sandwiching a thin and homogeneous layer of the alkene between the substrate and the quartz wall. The substrate was then illuminated with a hand-held 254 nm UV lamp (Model UVLS-28, UVP) for 30 minutes, followed by washing sequentially with petroleum ether, ethanol, and $CH_2Cl_2$, and finally drying with a stream of $N_2$.

EXAMPLE 4

This example serves to illustrate how Si surface type can affect the stability of the resulting nanometric biomolecular array.

Resistance comparisons between the adsorption and stability of OEG-terminated thin films on H—Si (100) and Si (111) were performed using the method as described in the present invention. Results indicated that the films of α-hepta-(ethylene glycol) methyl ω-undecenyl ether, $EG_7$, on Si (111) and (100) substrates reduced adsorption of protein (fibrinogen) by >99%. The films were stable under a wide range of conditions, such as in biological buffers at pH 7.4 and 9.0 (37° C.), water (100° C.), and 2.5 M $H_2SO_4$ (100° C.). The films derived on Si (111) were more stable than those on Si (100). Furthermore, it was demonstrated that the films on Si (100) or Si (111) could be patterned by AFM anodization lithography by the method as described in the present invention. The resultant patterns may serve as templates for directing the self-assembly of biomolecules such as fibrinogen, avidin, and bovine serum albumin (BSA) on the surfaces. See Yam et al., J. Colloid Interface Sci., 2005, in press.

EXAMPLE 5

This example serves to illustrate AFM anodization lithography on $EG_7$-coated Si (100) or Si (111) substrates, in accordance with embodiments of the present invention.

Figure 5:
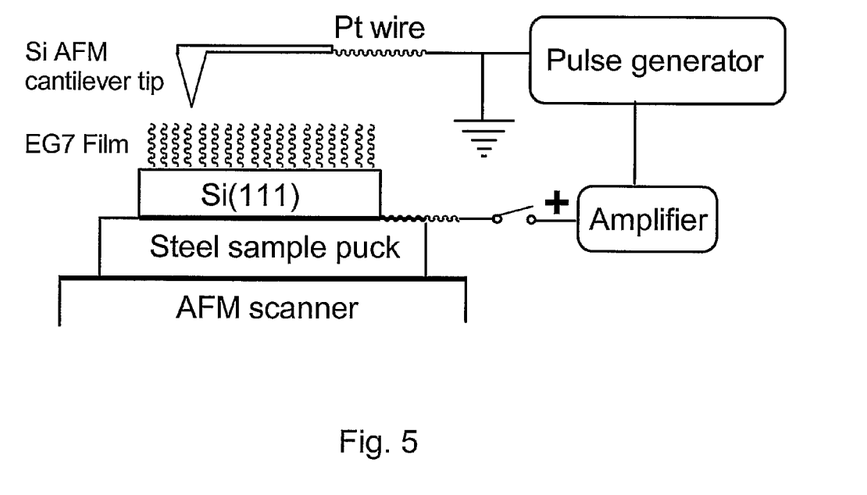
FIG. 5 illustrates a setup for AFM anodization lithography, in accordance with embodiments of the present invention.
Figure 6:
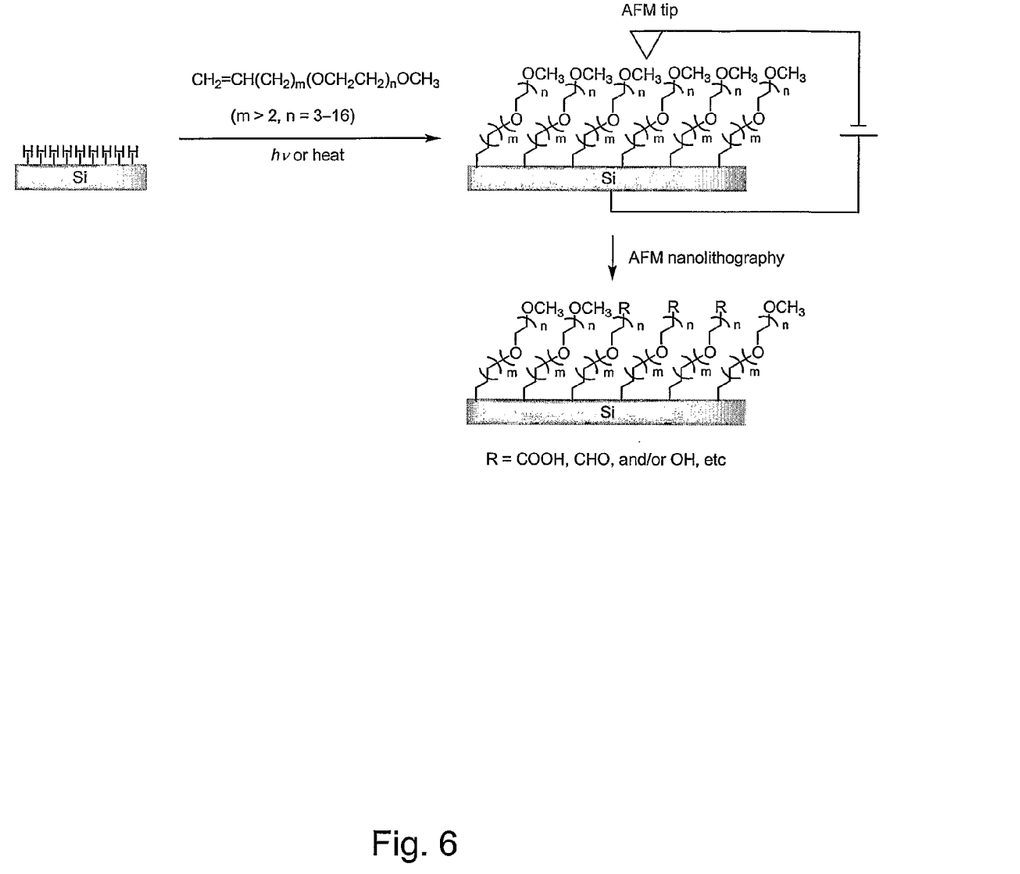
FIG. 6 illustrates AFM anodization lithography of an OEG monolayer on a Si surface, wherein the patterned (anodized) regions comprise functional moieties such as carboxylic acid, aldehyde, and/or alcohol, etc.

A setup for performing AFM anodization lithography on $EG_7$-coated Si (100) or Si (111) substrates, in accordance with embodiments of the present invention, is illustrated in FIG. 5. An OEG-coated silicon (100) or silicon (111) wafer was mounted on a steel sample puck using a double-sided carbon conductive tape that was also used to attach a short, thin Pt wire (25 µm in diameter). Another short, thin Pt wire was connected to the metal clip of a tip holder. The use of thin wires for electrical connection to the wafer and tip greatly reduces the vibration introduced to the system. Both Pt wires were connected through a BNC cable to a digital delay/pulse generator equipped with a homemade amplifier. The steel sample puck was mounted onto the AFM scanner that was insulated with a thin parafilm. AFM anodization lithograpy was performed under ambient conditions with a relative humidity of 25-55%, using a silicon cantilever with a force constant of 0.3 N/m and resistivity of ~0.08 ohm·cm. During scanning of the sample in contact mode (load: ~1 nN; scan size: 5×5 µm; scan rate: 29.8 µm/s), bursts of 10 pulses of +17 V square waves (pulse duration: 1 µs; interval between two pulses: 8.33 ms; interval between two bursts: 4.29 seconds) were applied to the sample while the tip was grounded. The nanolithography was completed in one scan, taking 85 seconds. For relocation of the nanopatterned areas after subsequent ex situ treatment of the sample, a tiny X mark with a line width of ~8 µm was drawn on the substrate with a diamond pen before nanolithgraphy, and the position of the cantilever relative to the mark shown by the CCD camera of the AFM was recorded FIG. 6 illustrates the above-described AFM anodization lithography of an OEG monolayer on a Si surface, wherein the patterned (anodized) regions comprise carboxylic acid moieties.

EXAMPLE 6

This example serves to illustrate AFM imaging, in accordance with embodiments of the present invention.

After nanolithography, the pulse generator was disconnected, and topography and friction AFM images were simultaneously acquired in contact mode at 90° scan angle with the same tip used for nanolithography. For imaging protein-coated surfaces, a soft cantilever with a force constant of 0.03 N/m was used at a loading force of ~1 nN.

EXAMPLE 7

This example serves to illustrate derivatization of the nanoarrays with biomolecules, in accordance with embodiments of the present invention.

The patterned substrates were treated sequentially with (a) a solution of succinic anhydride (100 mg), and DMAP (12 mg) in pyridine (1 ml) for 30 minutes; (b) a solution of EDAC (1 mg) and avidin (0.1 mg) in PBS (1 ml) for 5 minutes; (c) BSA (1 mg) in PBS (1 ml) for 5 minutes; (d) biotin-BSA (1 mg) in PBS (1 ml) for 5 minutes; (e) avidin (0.1 mg) in PBS (1 ml) for 5 minutes; and (f) proteinase K (1 mg) in PBS (1 ml) for 3 hours. All treatments were carried out under ambient conditions. After each step, the substrates were thoroughly washed with Millipore water, dried with a stream of $N_2$, and immediately imaged by AFM.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method comprising the steps of:
   a) contacting OEG-terminated alkenes with a hydrogen-terminated Si surface to form a contacted surface; wherein the OEG-terminated alkenes comprise α-heptyl-(ethylene glycol) methyl ω-undecenyl ether, wherein the Si surface is selected from the group consisting of Si(100), Si(111), and combinations thereof;
   b) photolyzing the contacted surface to effect Si—C bonding between the OEG-terminated alkenes and the Si surface and form a OEG-coated Si surface comprising a monolayer of OEG bound to the Si surface through Si—C bonds, wherein the monolayer of OEG resists non-specific adsorption of biomolecules with greater than 99% reduction in adsorption with respect to the Si surface;
   c) lithographically anodizing the head groups of the OEG monolayer of the OEG-coated Si surface via AFM anodization lithography to yield a nanolithographically-patterned OEG-coated Si surface, wherein the nanolithographically-patterned regions are further etched to form nanoholes, wherein the nanoholes comprise regions with enhanced associability toward biomolecules, wherein the nanolithographically-patterned regions resist denaturing of biomolecules; and
   d) depositing at least one type of biomolecule in the nanolithographically-patterned regions of enhanced associability to form a nanometric biomolecular array.

2. The method of claim 1, wherein the Si surface is atomically flat.

3. The method of claim 1, further comprising a step of washing the OEG-coated Si surface prior to lithographically anodizing regions on top of it.

4. The method of claim 1, wherein the nanolithographically-patterned regions of the OEG-coated Si surface comprise nanowells.

5. The method of claim 1, wherein the nanolithographically-patterned regions comprise functional moieties selected from the group consisting of carboxylic acid, aldehyde, hydroxyl, and combinations thereof.

6. The method of claim 5, wherein the functional moieties provide, at least in part, the enhanced associability toward biomolecules.

7. The method of claim 1, wherein the nanolithographically patterned regions of the OEG-coated Si surface comprise hydroxyl moieties that can be converted into carboxylic acid moieties.

8. The method of claim 1, wherein the at least one type of biomolecule is selected from the group consisting of proteins, oligonucleotides, and combinations thereof.

9. The method of claim 1, wherein the at least one type of biomolecule comprises avidin.

10. The method of claim 1, wherein at least some of the at least one type of biomolecule binds with the regions with enhanced associability via amide bonds.

11. The method of claim 1, further comprising the steps of:
a) depositing biomolecular analyte; and
b) analyzing the array to determine the regions in which the biomolecular analyte exhibits a binding affinity.

12. The method of claim 11, further comprising a step of regenerating the nanolithographically-patterned OEG-coated Si surface comprising regions with enhanced associability toward biomolecules by treatment of said surface with proteinase K, wherein the proteinase K serves to catalyze hydrolytic fragmentation of proteins bound to said surface.

* * * * *